US006225489B1

(12) United States Patent
Fost et al.

(10) Patent No.: US 6,225,489 B1
(45) Date of Patent: May 1, 2001

(54) SILICONE MODIFIED PHOSPHOLIPID COMPOSITIONS

(75) Inventors: Dennis L. Fost, Ridgewood; Abe Berger, Summit, both of NJ (US)

(73) Assignee: Mona Industries, Inc., Paterson, NJ (US)

( * ) Notice: Subject to any disclaimer, the term of this patent is extended or adjusted under 35 U.S.C. 154(b) by 0 days.

(21) Appl. No.: 08/358,207

(22) Filed: Dec. 16, 1994

Related U.S. Application Data

(63) Continuation-in-part of application No. 08/174,934, filed on Dec. 28, 1993, now Pat. No. 5,405,983, and a continuation-in-part of application No. 08/265,011, filed on Jun. 23, 1994, now abandoned.

(51) Int. Cl.$^7$ ............................................. C07F 7/10

(52) U.S. Cl. .............. 556/405; 554/39; 554/77; 546/14; 548/110; 549/214

(58) Field of Search ................ 556/405; 549/214; 548/120; 546/14; 554/39, 77

(56) References Cited

U.S. PATENT DOCUMENTS

| | | |
|---|---|---|
| 2,488,449 | 11/1949 | Trautman . |
| 2,768,193 | 10/1956 | Gilbert . |
| 2,843,615 | 7/1958 | Linville . |
| 3,067,229 | 12/1962 | Fekete . |
| 3,113,139 | 12/1963 | Birum et al. . |
| 3,389,160 | 6/1968 | Reid . |
| 3,441,537 | 4/1969 | Lengnick . |
| 3,492,193 | 1/1970 | Tesoro . |
| 3,716,569 | 2/1973 | Redmore et al. . |
| 3,839,388 | 10/1974 | Nitzsche et al. . |
| 3,890,269 | 6/1975 | Martin . |
| 4,006,176 | 2/1977 | Heckert et al. . |
| 4,045,460 | 8/1977 | Kleinstuck . |
| 4,093,641 | 6/1978 | Plueddemann . |
| 4,104,296 | 8/1978 | Pike . |
| 4,185,087 | 1/1980 | Morlino . |

(List continued on next page.)

Primary Examiner—Paul F. Shaver
(74) Attorney, Agent, or Firm—Franklyn Schoenberg; Norman E. Lehrer

(57) ABSTRACT

Phospholipid compositions that may be represented by the following general formula:

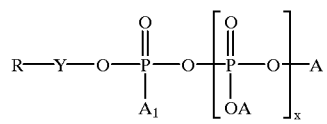

wherein:

A is selected from H, M, and R—Y—;

$A_1$ is selected from H, OH, OM and R—Y—O—;

x is 0 or an integer from 1 to 5;

M is a cation;

Y is alkylene or substitued alkylene; and

R is a mixture of quaternized amidoamine and/or amine moieties selected from the group consisting of:

a) a quaternized organosilicone amidoamine moiety of the formula:

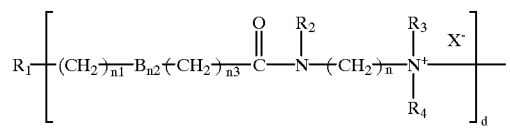

b) a quaternized organosilicone tertiary amine moiety of the formula:

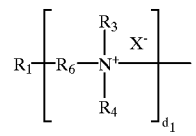

or a mixture of the quaternized organosilicone amidoamine moiety "a" and/or quaternized tertiary amine moiety "b" above and the moieties:

c) a quaternized organic amidoamine moiety of the formula:

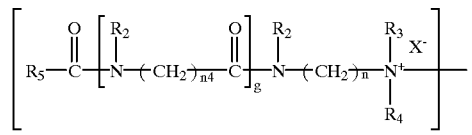

d) an organic quaternized tertiary amine moiety of the formula:

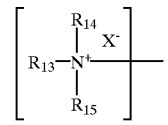

with the proviso that wherein R is a mixture of organosilicone amine and organic amine moieties, at least 5 equivalent weight percent to about 60 equivalent weight percent of the total equivalent weight of amine moieties of the phospholipid composition is a quaternized organosilicone amidoamine moiety, a quaternized organosilicone tertiary amine moiety or mixtures of the same.

12 Claims, No Drawings

U.S. PATENT DOCUMENTS

| | | |
|---|---|---|
| 4,234,502 | 11/1980 | Kappler et al. . |
| 4,282,366 | 8/1981 | Eudy . |
| 4,342,742 | 8/1982 | Sebaq et al. . |
| 4,384,130 | 5/1983 | Martin . |
| 4,417,066 | 11/1983 | Westall . |
| 4,511,727 | 4/1985 | Martin . |
| 4,654,161 | 3/1987 | Kollmeier et al. . |
| 4,847,397 | 7/1989 | Sawaragi et al. . |
| 4,866,192 | 9/1989 | Plueddemann et al. . |
| 4,889,942 | 12/1989 | Gutek et al. . |
| 4,891,166 | 1/1990 | Schaefer et al. . |
| 4,898,614 | 2/1990 | Halloran et al. . |
| 4,900,857 | 2/1990 | Klett . |
| 4,996,342 | 2/1991 | Ching et al. . |
| 5,008,424 | 4/1991 | Halloran et al. . |
| 5,039,761 | 8/1991 | Ono et al. . |
| 5,068,377 | 11/1991 | Kawamoto et al. . |
| 5,070,171 | 12/1991 | O'Lenick, Jr. . |
| 5,087,715 | 2/1992 | Snow . |
| 5,091,493 | 2/1992 | O'Lenick, Jr. et al. . |
| 5,093,452 | 3/1992 | O'Lenick, Jr. . |
| 5,099,051 | 3/1992 | Beck et al. . |
| 5,101,056 | 3/1992 | Kampling et al. . |
| 5,137,951 | 8/1992 | Pastor et al. . |
| 5,151,210 | 9/1992 | Steurii et al. . |
| 5,405,983 * | 4/1995 | Fost et al. .............................. 556/405 |

* cited by examiner

SILICONE MODIFIED PHOSPHOLIPID COMPOSITIONS

RELATED APPLICATIONS

This application is a continuation in part of application Ser. No. 08/174,934 filed Dec. 28, 1993 now U.S. Pat. No. 5,405,983 and application Ser. No. 08/265,011 filed Jun. 23, 1994 now abandoned.

FIELD OF THE INVENTION

The present invention relates to novel organosilicone compounds and, more particularly, to silicone containing derivatives having at least one esterified phosphate group in the molecule.

BACKGROUND OF THE INVENTION

Phosphate esters, quaternary amine compounds, betaines and certain substituted betaines are known in the art and have been commercially used over the years for a variety of applications, including those requiring surfactant properties. More recently, various betaine derivatives having, in general, specific quaternary compounds linked to phosphate esters referred to as phosphobetaines, and more particularly "synthetic phospholipids," have been disclosed, for example, in U.S. Pat. Nos. 4,215,064, 4,233,192, 4,380,637 and 4,382,036 to Lindemann et al.; U.S. Pat. Nos. 4,209,449, 4,336,385 and 4,503,002 to Mayhew et al.; U.S. Pat. Nos. 4,243,602, 4,283,542 and 4,336,386 to O'Lenick et al; and U.S. Pat. No. 4,617,404 to Lukenbach et al. These synthetic phospholipids are disclosed as exhibiting outstanding foaming, viscosity building, wetting, cleansing, detergency, anti-static, conditioning and emulsifying properties, making them useful in industrial applications calling for high performance surface active agents. The synthetic phospholipids are also described as being highly stable compositions which are well tolerated by human tissue (i.e. they exhibit exceptionally low oral toxicity and ocular irritation) and, hence, are well suited for use in a variety of personal care applications including cosmetic formulations as well as in industrial processes.

A variety of organosiloxane compositions including compositions which exhibit excellent properties as surface active agents, lubricants and the like are well known and have been used commercially over the years, including for personal care and home care applications. In general, organosiloxane compositions are water-insoluble and the costs thereof are greater than many other commercial materials which has limited their use for many applications. Recently, particular types of betaine and phosphobetaine modified organosiloxanes have been disclosed, for example, in U.S. Pat. Nos. 4,609,750 and 4,654,161 to Kollmeier et al. and U.S. Pat. No. 5,091,493 to O'Lenick et al which have been suggested as exhibiting high foaming characteristics in water, substantivity to a variety of surfaces, reduced irritation to the eyes and skin and improved, although limited, water-solubility properties. While, as indicated, certain organosilicone compositions containing phosphobetaines and methods for preparing the same have been suggested, there has been no prior disclosure or suggestion of the novel silicone modified phospholipid compositions and preparation methods described in copending application Ser. No. 174,934, of which the present application is a continuation in part, or of the novel silicone modified phospholipid compositions and methods for preparing the same herein described which compositions exhibit a greater range of properties for different applications as well as providing means for closer control of the costs of the organosilicone products.

SUMMARY OF THE INVENTION

It is accordingly an object of the present invention to provide novel silicone-modified phospholipid compositions suitable for use in solvent and/or preferably aqueous based systems which exhibit excellent surface-active properties including high foaming, are well tolerated by human tissue, are substantive to the surface of natural and synthetic fiber, and the like.

It is another object of the present invention to provide novel water-soluble silicone-modified phospholipid compositions containing terminal, lateral (pendant) or combinations of terminal and lateral (pendant) silicone moieties and wherein the compositions can be prepared with a variety of concentrations of silicone as desired or required.

In accordance with the present invention, there has now been discovered novel phospholipid compositions that may be represented by the following general formula:

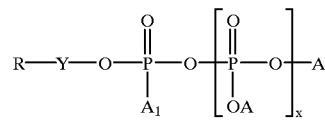

wherein:

A is selected from H, M, and R—Y—;

$A_1$ is selected from H, OH, OM, and R—Y—O—;

x is o or an interger from 1 to 5;

M is a cation, preferably an alkali metal;

Y is alkylene or substitued alkylene; and

R is selected from;

a) a quaternized organosilicone amidoamine moiety of the formula:

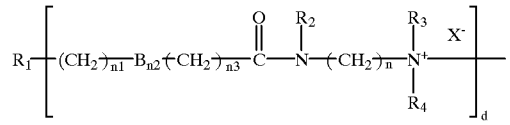

wherein:

$R_1$ is a silicone backbone chain as hereinafter described to which amidoamine and/or amine functional group(s) as herein described can be attached;

$R_2$ is hydrogen or alkyl, hydroxyalkyl or alkenyl of up to 6 carbon atoms each, or cycloalkyl of up to 6 carbon atoms, or polyoxyalkylene of up to 10 carbon atoms preferably from 2 to 5 carbon atoms within the oxyalkylene unit;

$R_3$ and $R_4$, which may be the same or different, are selected from alkyl, hydroxyalkyl, carboxyalkyl of up to 6 carbon atoms in each alkyl, and polyoxyalkylene of up to 10 carbon atoms;

$X^-$ is an anion, preferably a halogen;

n is an integer from 2 to 12;

$n^1$ is zero or an integer from 1 to 12;

$n^2$ is 0 or 1;

$n^3$ is an integer from 1 to 5;

B is sulfur (S) or oxygen (O); with the proviso that when $n^2$ is 0, $n^1$ or $n^3$ is at least 1 and when $n^2$ is 1, $n^1$ and $n^3$ each is at least 1; and d is one or greater, preferably 2–10;

b) a quaternized organosilicone tertiary amine moiety of the formula:

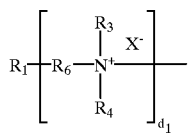

wherein:

$R_1$ is a silicone backbone claim as hereinafter described to which amidoamine and/or amine functional groups can be attached;

$R_6$ is alkylene, hydroxyalkylene, arylene, alkarylene, aralkylene, heteroalkylene wherein the heteroatom can be N, S or O and there can be more than one of such hetero atoms in the chain;

$X^-$ is an anion, preferably a halogen;

$d^1$ is an integer of one or greater, preferably from 2 to 10; and $R_3$ and $R_4$ are as hereinabove defined;

or a mixture of the quaternized organosilicone amidoamine moiety "a" and/or quaternized tertiary amine moiety "b" above and the moieties:

c) a quaternized organic amidoamine moiety of the formula:

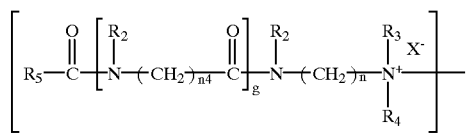

wherein:

$R_5$ is alkyl, alkenyl, alkoxyalkyl or hydroxyalkyl of from 5 to 21 carbon atoms each, alkaryl or aryl of up to 20 carbon atoms;

$R_2$ is hydrogen or alkyl, hydroxyalkyl or alkenyl of up to 6 carbon atoms each, cycloalkyl of up to 6 carbon atoms, or polyoxyalkylene of up to 10 carbon atoms, preferably of from 2 to 5 carbon atoms, within the oxyalkylene unit;

$R_3$ and $R_4$ which may be the same or different, are selected from alkyl, hydroxyalkyl, carboxyalkyl of up to 6 carbon atoms in each alkyl moiety, and polyoxyalkylene of up to 10 carbon atoms; in addition $R_3$ and $R_4$ taken together with the nitrogen to which they are attached may represent an N-heterocycle;

$X^-$ is an anion, preferably a halogen;

g is 0 or 1;

n is integer from 2 to 12; and $n^4$ is 1 or greater; and/or d) an organic quaternized tertiary amine moiety of the formula:

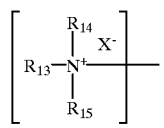

wherein:

$R_{13}$, $R_{14}$ and $R_{15}$ are the same or different and are alkyl, substituted alkyl, alkyl aryl or alkenyl groups of up to 16 carbon atoms with the proviso that the total carbon atoms in $R_{13}+R_{14}+R_{15}$ is between 10 and 24;

with the proviso that wherein R is a mixture of organosilicone amine and organic amine moieties, at least 5 equivalent weight percent to about 60 equivalent weight percent of the total equivalent weight of amine moieties of the phospholipid composition is a quaternized organosilicone amidoamine moiety, a quaternized organosilicone tertiary amine moiety or mixtures of the same.

The silicone backbone chain, $R_1$, to which the amidoamine and/or amine functional groups as herein described are attached and which are shown herein as $R_{11}$, corresponds to the general formula:

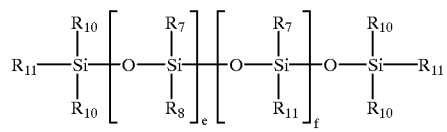

wherein:

$R_7$ and $R_8$, which may be the same or different are selected from alkyl, aryl, capped or uncapped polyoxyalkylene, alkaryl, aralkylene and alkenyl (vinyl);

$R_{10}$ can be the same or different and can be selected from alkyl, aryl and olefinic (vinyl);

$R_{11}$, which can be the same or different, can be selected from $R_{10}$, $-(CH_2)_{n1}-B_{n2}-(CH_2)_{n3}-CO-NR_2-(CH_2)_n-NR_3R_4$, $-R_6-NR_3R_4-$ and mixtures thereof, wherein $R_2$, $R_3$, $R_4$, $R_6$, B, n, $n^1$, $n^2$ and $n^3$ are as defined above; with the proviso that at least one of $R_{11}$ is an amidoamine or tertiary amine;

e can be an integer of 0 to 50,000;

f can be an integer of 0 to 100.

It is evident from the above general formula for phospholipid compositions of the invention that the functional phosphorus containing group(s) can be linked terminally, laterally or both terminally and laterally to the siloxane backbone chain.

In another aspect of the present invention there is provided a method of preparing novel phospholipid compositions that may be represented by the general formula:

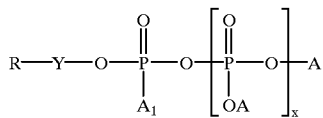

wherein:

A is selected from H, M, and R—Y—;

$A_1$ is selected from H, OH, OM, and R—Y—O—;

M is a cation, preferably an alkali metal;

x is 0 or an integer from 1 to 5;

Y is alkylene or substituted alkylene; and

R is a mixture of quaternized amidoamine and/or tertiary amine moieties as hereinabove defined;

which comprises reacting the combination of an organic amidoamine and/or organic tertiary amine reactant and a silicone modified amidoamine and/or silicone modified tertiary amine reactant with a polyphosphate, phosphite or phosphate ester reactant in the equivalent weight ratios of from about 0.7 to 3.3, of total amidoamine and/or tertiary amine reactants to 1 of polyphosphate, phosphite or phosphate ester halide reactant until the amine reactant is completely reacted, with the proviso that at least 5 equivalent weight percent to about 60 equivalent weight percent of the total equivalent weight of amine reactants will be silicone containing, said polyphosphate, phosphite or phosphate ester halide reactant being of the general formula:

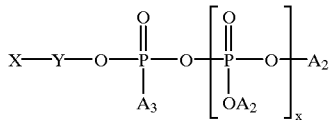

wherein:

$A_2$, is selected from H, M and X—Y—;

$A_3$ is selected from H, OH, OM, and R—Y—O—;

x is O or an integer from 1 to 5;

M is a cation, preferably alkali metal;

Y is alkylene or substituted alkylene; and

X is halogen.

DESCRIPTION OF THE PREFERRED EMBODIMENTS

The novel phospholipid compositions of the present invention comprise a class of compositions which may be represented by the general formula:

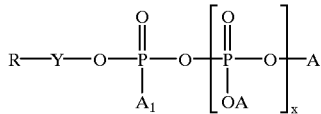

wherein:

A is selected from H, M, and R—Y—;

$A_1$ is selected from H, OH, OM and R—Y—O—;

x is O or an integer from 1 to 5;

M is a cation, preferably an alkali metal;

Y may be alkylene, optionally interrupted by up to 3 oxygen atoms, of up to 12 carbon atoms, which alkylene chain may optionally be substituted with lower alkyl, alkoxyalkyl or hydroxyalkyl, e.g., of not more than 10 carbon atoms each;

R is selected from:

a) a quaternized organosilicone amidoamine moiety of the formula:

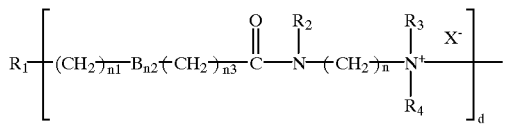

wherein:

$R_1$ is a silicone backbone chain hereinafter described to which amido amine functional group(s) as herein described can be attached;

$R_2$ is hydrogen or alkyl, hydroxyalkyl or alkenyl of up to 6 carbon atoms each, or cycloalkyl of up to 6 carbon atoms, or polyoxyalkylene of up 10 to 10 carbon atoms, preferably from 2 to 5 carbon atoms, within the oxyalkylene unit;

$R_3$ and $R_4$, which may be the same or different, are selected from alkyl, hydroxyalkyl, carboxyalkyl of up to 6 carbon atoms in each alkyl, and polyoxyalkylene of up to 10 carbon atoms;

$X^-$ is an anion, preferably a halogen;

n is an integer from 2 to 12;

$n^1$ is zero or an integer from 1 to 12;

$n^2$ is 0 or 1;

$n^3$ is an integer from 1 to 5;

B is sulfur (S) or oxygen (O); with the proviso that when $n^2$ is 0, $n^1$ or $n^3$ is at least 1 and when $n^2$ is 1, $n^1$ and $n^3$ each is at least 1; and d is one or greater, preferably 2–10;

b) a quaternized organosilicone tertiary amine moiety of the formula:

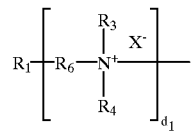

wherein:

$R_1$ is a silicone backbone claim as hereinafter described to which amine functional groups can be attached;

$R_6$ is alkylene, hydroxyalkylene, arylene, alkarylene, aralkylene, heteroalkylene wherein the heteroatom can be N, S or O and there can be more than one of such hetero atoms in the chain;

$X^-$ is an anion, preferably a halogen;

$d^1$ is an integer of one or greater, preferably from 2 to 10; and $R_3$ and $R_4$ are as hereinabove defined;

or a mixture of the quaternized organosilicone amidoamine moiety "a" and/or quaternized organosilicone tertiary amine moiety "b" above and moieties selected from the group consisting of:

c) a quaternized organic amidoamine moiety of the formula:

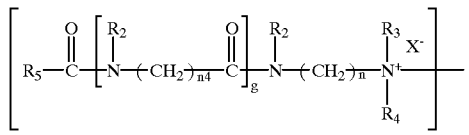

wherein:

$R_5$ is alkyl, alkenyl, alkoxyalkyl or hydroxyalkyl of from 5 to 21 carbon atoms each, alkaryl or aryl of up to 20 carbon atoms;

$R_2$ is hydrogen or alkyl, hydroxyalkyl or alkenyl of up to 6 carbon atoms each, cycoalkyl of up to 6 carbon atoms, or polyoxyalkylene of up to 10 carbon atoms, preferably of from 2 to 5 carbon atoms within the oxyalkylene unit;

$R_3$ and $R_4$ which may be the same or different, are selected from alkyl, hydroxyalkyl, carboxyalkyl of up to 6 carbon atoms in each alkyl moiety, and polyoxyalkylene of up to 10 carbon atoms; in addition $R_3$ and $R_4$ taken together with the nitrogen to which they are attached may represent an N-heterocycle;

$X^-$ is an anion, preferably a halogen;

g is 0 or 1 n is integer from 2 to 12; and $n^4$ is an 1 or greater; and/or d) an organic quaternized tertiary amine moiety of the formula:

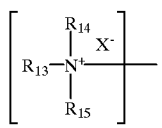

wherein:
  $R_{13}$, $R_{14}$ and $R_{15}$ are the same or different and are alkyl, substituted alkyl, alkaryl or alkenyl groups of up to 16 carbon atoms with the proviso that the total carbon atoms in $R_{13}+R_{14}+R_{15}$ is between 10 and 24;
  x– is an anion, preferably a halogen.
with the proviso that wherein R is a mixture of organosilicone amine and organic amine moieties, at least 5 equivalent weight percent to about 60 equivalent weight percent of the total equivalent weight of amine moieties of the phospholipid composition is a quaternized organosilicone amidoamine moiety, a quaternized organosilicone tertiary amine moiety or mixtures of the same.

A preferred phopholipid composition of the invention wherein Y is 2-hydroxypropylene comprises a class of compositions which may be represented by the general formula:

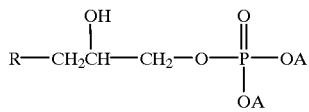

wherein
  A and R are as defined hereinabove.

The silicone backbone chain $R_1$ to which the amine functional groups as hereinabove shown are attached and which are shown herein as $R_{11}$, corresponds to the general formula:

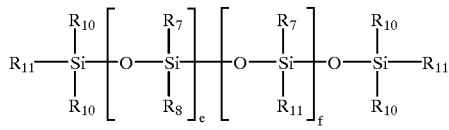

wherein:
  $R_7$ and $R_8$, which may be the same or different are selected from alkyl, aryl, capped or uncapped polyoxyalkylene, alkaryl, aralkylene and alkenyl (vinyl);
  $R_{10}$ can be the same or different and can be selected from alkyl, aryl and olefinic (vinyl);
  $R_{11}$, which can be the same or different, may be selected from $R_{10}$, $-(CH_2)_{n1}-B_{n2}-(CH_2)_{n3}CO-NR_2-(CH_2)_n-NR_3R_4-$, $-R_6-NR_3R_4-$ and mixtures thereof wherein $R_2$, $R_3$, $R_4$, $R_6$, B, n, $n^1$, $n^2$ and $n^3$ are as defined above; with the proviso that at least one of $R_{11}$ is an amidoamine or tertiary amine;
  e can be an integer of O to 50,000;
  f can be an integer of 0 to 100.

It is evident from the general formula of the novel phospholipid compositions of the invention that the functional phosphorus containing group(s) can be linked terminally, laterally or both terminally and laterally to the siloxane chain.

The phospholipid compositions of the invention can be prepared by reacting corresponding silicone-modified tertiary amine and/or amidoamine reactants or combinations of corresponding silicone modified tertiary amine and/or amidoamine reactants and organic tertiary amine and/or amidoamines reactants with polyphosphate, phosphite, or phosphate ester halide reactants in appropriate stoichiometric quantities as will be described in detail hereinafter to obtain the desired products of the formula:

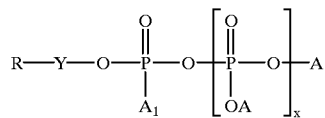

and preferably

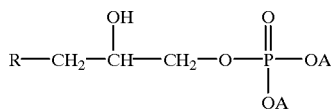

wherein:
  A is as defined hereinabove;
  $A_1$ is as defined hereinabove;
  x is as defined hereinabove;
  M is as defined hereinabove;
  R is selected from a quaternized organosilicone amidoamine moiety, a quaternized organosilicone tertiary amine moiety, or a mixture of moieties selected from a quaternized organosilicone amidoamine moiety, a quaternized organosilicone tertiary amine moiety, an organic amidoamine or organic tertiary amine moiety or mixtures thereofas defined hereinabove; with the proviso that wherein R is a mixture of organosilicone amine and organoamine moieties at least 5 to about 60 equivalent weight percent of the total equivalent weight of amine moieties of the phospholipid composition is a quaternized organosilicone amidoamine, a quaternized organosilicone tertiary amine and mixtures of the same.

The intermediate reactants required in the processes for preparing the phospholipid compositions of the invention can be prepared as follows:

Phosphate, polyphosphate and/or phosphite ester halide intermediate reactants based on epichlorhydrin can be prepared by known procedures illustrated as follows:

I

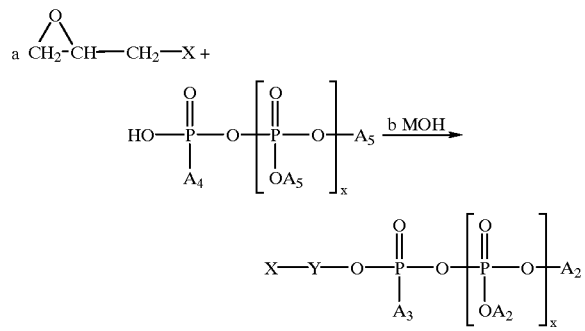

wherein:
  $A_2$ is selected from H, M and X—Y—;

$A_3$ is selected from H, OH, OM and X—Y—O—;

$A_4$ is H, OM or OH;

$A_5$ is H or M;

a is from 0.5 to 3.5, preferably 1 to 3;

b is from 1 to 3, preferably 1–2;

X is 0 or an integer from 1–5;

M is a cation, preferably alkali metal;

x is halogen;

Y is 2 hydroxyproplyene.

The above coupling reaction is carried out in an aqueous media, preferably in the range of 30–50% concentration, having a pH range of 5.0–8.0.

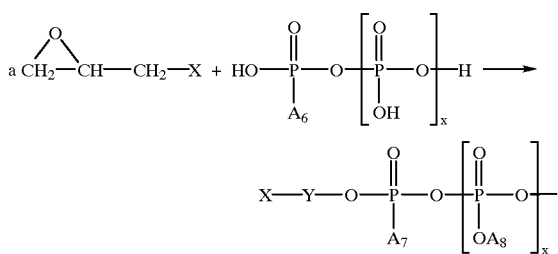

II wherein:

$A_7$ is H, OH or X—Y—O—;

$A_8$ is H or —Y—X;

a is from about 0.5 to 7, preferably, from about 1 to 3;

x is 0 or an integer from 1–5;

X is halogen;

Y is 2 hydroxypropylene.

The reaction is preferably carried out in absence of water with slight excess epichlorohydrin.

Phosphate, phosphite and/or polyphosphate ester intermediate reactants for preparing phosphobetaine, pyrophosphobetaine and the like compositions of the invention can also be prepared by known procedures such as are disclosed, for example, in U.S. Pat. No. 4,617,414.

Silicone-modified amidoamine intermediate reactants suitable for use in preparing the phospholipid composition of the invention can be prepared as follows:

Also suitable as phosphate and phosphite intermediate reactants are such reactants prepared by known procedures illustrated as follows:

III (a)

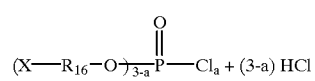

III (b)

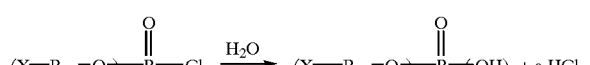

wherein a is 0 or an integer from 1 to 2;

X is halogen, preferably bromine;

$R_{16}$ is alkylene.

IV (a)

IV (b)

wherein

X is a halogen, preferably bromine;

$R_{16}$ is alkylene.

Carrying out reactions III(a) and IV(b) in presence of a tertiary amine HCl acceptor is preferred to prevent formation of free acid.

Silicone-modified amidoamine intermediate reactants suitable for use in preparing the phospholipid composition of the invention can be prepared as follows:

V

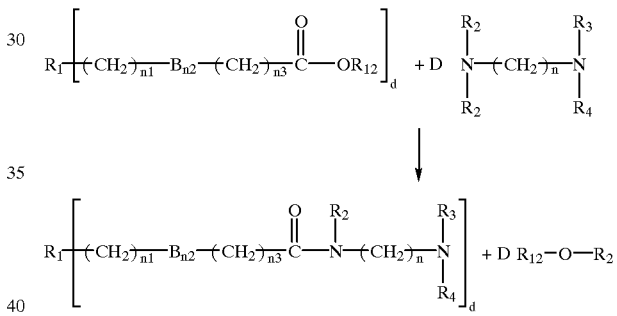

wherein:

$R_1$ is a silicone backbone chain as herein defined;

$R_2$ is as hereinabove defined;

$R_3$ and $R_4$ is as previously defined;

$R_{12}$ is hydrogen or alkyl;

B is sulfur or oxygen; with the proviso that when $n^2$ is 0, $n^1$ or $n^3$ is at least 1 and when $n^2$ is 1, $n^1$ and $n^3$ each is at least 1;

n is an integer from 2 to 12;

$n^1$ is zero or an integer of one or greater;

$n^2$ is 0 or 1;

$n^3$ is an integer of 1 to 5;

d and D is an integer from 1 or greater, generally from 1–50 and preferably 2–10. The reactant ratio of the amine reactant to the carboxyl reactant on the silicon is preferably 1:1 but can be varied in ratio of 0.8–1.2.

The above coupling reaction (V) for preparing the silicone-modified amidoamine intermediate reactants can be carried out neat or can be carried out in an inert solvent such as xylene, toluene, benzene, chlorobenzene or the like.

The polysiloxane-containing functional carboxylic acids or derivatives thereof (terminal, lateral or combination of terminal and lateral) applicable for use in preparing the silicone-modified amidoamine intermediate reactants as set forth in the reaction sequence illustrated above (III) can be prepared by a variety of known procedures such as illustrated by the following:

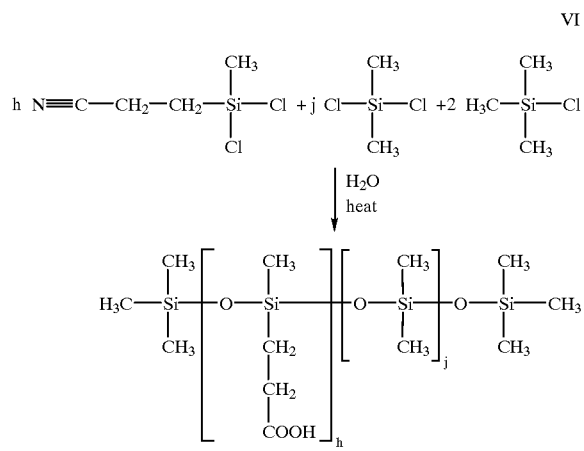

wherein:
h is an integer from 1–100;
j is an integer from 0–1000.

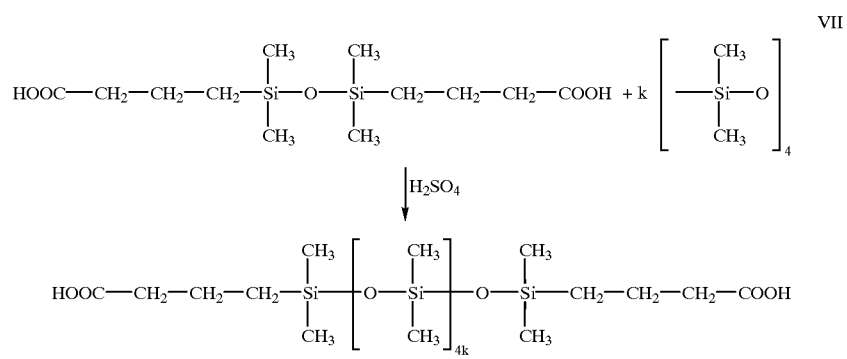

wherein:
k is an integer from 1–1000.

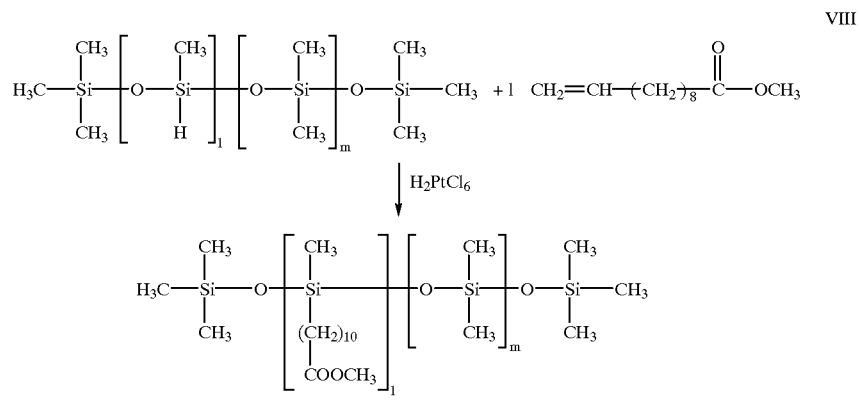

wherein:
l is an integer from 1–100;
m is an integer from 0–1000.

Suitable carboxyl functional silicone compositions having terminal, lateral or combinations of terminal and lateral functional groups are available commercially, for example, from Shin-Etsu. While the molecular weight of the silicone compositions which may be employed are not critical, and suitable compositions may have amine equivalent weights of 8000, or even higher, silicone compositions having amine equivalent weights from about 1500 to about 6000 are in general preferred.

Silicone-modified tertiary amine intermediate reactants which are suitable for use in preparing alternate embodiments of the silicone-modified phospholipid compositions of the invention can be silicone-modified tertiary amines (terminal, lateral or combinations thereof) which are prepared by a variety of known procedures such as disclosed, for example, in U.S. Pat. No. 3,389,160 which describes the preparation of a carbinol containing tertiary silicone amine encompassing the reaction of a secondary amine with an epoxy containing silicone fluid (example 1) and by Snow et al, J. Langmuir, 1990, 6(2), pp 336–39, wherein the preparation of tertiary amino functional siloxanes result from the hydrosilylation of olefinic tertiary amines with hydride siloxane fluids employing a platinum catalyst.

In addition, the preparation of a suitable functional tertiary amino alkyl dimethylsilyl capped material is disclosed in U.S. Pat. No. 4,918,210, at example 1, part 2 which consists of the Pt catalyzed addition of a terminal hydride containing silicone fluid with N-allyl-diethylamine. In general, silicone containing tertiary amine intermediate reactants with molecular weights ranging, between about 1000 and 6000 are most advantageously employed.

The organic amidoamine intermediate reactants suitable for use in preparing the phospholipid compositions of the invention can be prepared as follows:

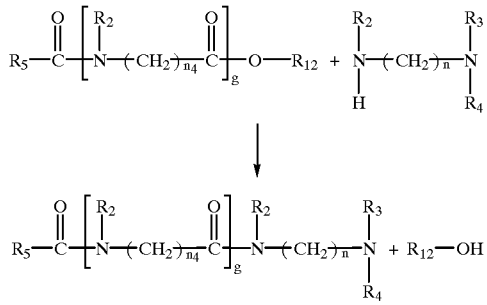

wherein:
$R_5$ is as hereinabove defined;
$R_2$ is as hereinabove defined;
$R_3$ and $R_4$ is as hereinabove defined;
$R_{12}$ is hydrogen or alkyl;
g is 0 or 1;
n is an integer from 2 to 12; and
$n^4$ is 1 or greater.

The organic amidoamine intermediate reactants suitable for use in preparing the phospholipid compositions shown in the above coupling reaction are known or are generally prepared in accordance with conventional techniques. A wide variety of commercially available tertiary amino alkyl amines are suitable for use in reaction with an acid or acid derivative to prepare suitable amidoamines, as are the amidoamines themselves. The suitable tertiary amino alkyl amines can be primary or secondary amines with the proviso that the total number of carbons in the acid portion of the molecule be greater than 6, i.e. to give a hydrophobic moiety necessary for surface activity properties. Suitable amidoamines include acyl derivatives of aminoacid products such as glycine and sarcosine (N-methylglycine) including for example, products available under the Tradename HAMPO-SYL from the Hampshire Chemical Co.

The organic tertiary amine reactants suitable for use in preparing the phospholipid compositions of the invention can be prepared using procedures well known in the art and many suitable compositions are available.

Exemplary tertiary amines include:
tributylamine
bis(hydroxyethyl)hexylamine
bis(2-hydroxyethyl)cocoamine
N,N-dimethyl-dodecylamine
N,N-dimethyl-tetradecylamine
N,N-dimethyl-hexadecylamine
N,N-dimethyl-cocoamine
N,N-dimethyl-cetylamine
dimethyl ($C_8$–$C_{16}$) alkyl amine.
N,N-dimethyl-octadecylamine As indicated, the phospholipid compositions of the invention can be prepared by reacting a tertiary amine or amidoamine functional silicones or combination of tertiary amine and/or amidoamine functional silicones and organic tertiary amine and/or amidoamine reactants with the phosphate ester halide reactants herein described in appropriate stoichiometric quantities as will be discussed in detail hereinafter.

The reaction of silicone containing amidoamine or tertiary amine functional groups with phosphate, polyphosphate and/or phosphite ester halide reactants in molar equivalents from about 0.7 to 3.3 of the amine functional silicones to 1 of the phosphate, phosphite and/or polyphosphate ester halide reactants based on the reaction can be readily carried out in an aqueous or aqueous organic co-solvent reaction systems wherein the number of grams of silicone fluid containing an amine equivalent lie in the area up to about 1200. Reactions will go to completion as demonstrated by chlorine analysis, alkali number titration, and homogeneity of reaction. When the number of grams of fluid per amine equivalent weight of the silicone reactants is greater than about 1200 to 2000 the reactants are partially or completely insoluble in the reaction system and an incomplete reaction will result. With silicone composition reactants having amine equivalent weights above about 2000, the addition of a co-solvent to an aqueous reaction system will not increase the solubility of the reactants as evidenced by phase separation and/or other signs of incomplete reaction. Surprisingly and unexpectedly, it has been found that phospholipid compositions of the invention can be prepared in substantial complete reaction form and in completely soluble reaction systems using tertiary amine and/or amidoamine functional silicone reactants having amine equivalent weights of 6000, or even greater, by also incorporating in the reaction system, organic tertiary amine and/or amidoamine reactants as herein described in conjunction with the functional silicone reactants. The organic tertiary amine and/or amidoamine reactant is added to the reaction system as a partial replacement of a molar equivalent amount of the functional silicone reactant, which substantially maintains the above noted molar equivalent ratios of amine reactants to phosphate ester halide reactants in the reaction mixture.

The reaction of a combination of organic tertiary amine and/or amidoamine reactants and silicone modified amine reactants with phosphate, phosphite and/or polyphosphate ester halide reactants will proceed to completion at an elevated temperature, preferably a temperature ranging from about 75° C. to 95° C., with the formation of the silicone-modified phospholipid compositions. The order of addition of the reactants is not critical and while a heterogeneous mixture may result when all reactants are admixed, the system becomes homogenous as the reaction proceeds. The reaction may start slowly while the mixture is heterogeneous but the reaction mixture will become substantially clear as the reaction proceeds. In accordance with the process of the invention, silicone-modified phospholipid compositions which contain at least 5 equivalent weight percent to about 60 equivalent weight percent silicone of the total amine containing moieties can be prepared, which silicone-containing phospholipid compositions will be completely soluble in aqueous/solvent or, preferably, aqueous systems while exhibiting surface active properties including low surface tension, high foaming and substantivity characteristics, low ocular and skin irritation and the like. Thus, it is possible by choice of particular amine functional silicone, organic amine and phosphate ester halide reactants to obtain soluble and preferably aqueous soluble silicone-modified phospholipid composition with a wide range of surface active agent properties for use in a variety of applications.

The preparation of specific compositions of the invention is illustrated by the following specific examples which are provided herein for purposes of illustration only and are not intended to limit the scope therein.

EXAMPLE 1

A carboxyl containing (pendant), trimethylsilyl capped silicone fluid obtained from Shin-Etsu under the designation X-22310 having a carboxyl content of 3.5% and an initial equivalent weight of 1289 is used in this example.

1592.7 grams (1.235 moles) of the above polysiloxane fluid is combined with 189 grams (50% excess) of dimethylaminopropyl amine (DMAPA) in a reaction vessel and heated slowly under nitrogen to about 185° C. The reaction is carried out for 4 hours while volatiles come off and are collected. There is collected a total of 44 ml of volatiles as two layers, the bottom layer of 25 ml is water with some volatilized dimethylaminopropyl amine. The residue in the reaction vessel has an acid number less than 1.

The materials are then heated to a temperature of 120°'–140° C. under a vacuum of 10 mm for 3 hours. At this point the polysiloxane/DMAPA reaction product is found to have an alkali number of 42 and equivalent weight of 1335.

264 grams (0.9428 moles) of cocoyl sarcosine obtained as HAMPOSYL C from Hampshire Chemical Corp. is reacted with 144 grams (an excess) of dimethylaminopropyl amine in 150 ml of refluxing xylene under a nitrogen atmosphere, with water being removed as it is formed. After 4 hours, water no longer evolves and the xylene and any volatiles are removed by heating the reaction mixture to 130° C. at 10 mm vacuum for 3 hours. 348 grams of a product having an alkali number of 185 is obtained.

2.7 grams (0.002 mole) of the above silicone/DMAPA product are combined with 2.4 grams (0.008 moles) of the above sarcosine/DMAPA product; 3.12 grams (0.0033 moles) of a 40% concentration of a phosphate ester halide reactant prepared by the reaction of 3 moles of epichlorohydrin with one mole of 85% phosphoric acid in the presence of one mole sodium hydroxide; and 13 grams water. The amidoamine reactants are used in an equivalent weight ratio of 4:1 of organic amidoamine to silicone amidoamine reactants.

The reaction mixture is heated for 3 hours at 90° C. at which time a hazy but homogeneous reaction product is obtained having a % NaCl content of 2.6 (2.8 theoretical).

The resultant product when added to water forms a clear solution which foamed well, as compared to the silicone fluid starting material which forms a hazy, non-foaming mixture in water.

EXAMPLE 2

6.67 grams (0.005) of a silicone/DMAPA reaction product (equivalent weight 1335) prepared as described in example 1 is mixed with 3.84 grams (0.010 mole) of the reaction product of linoleic acid and dimethylaminopropyl amine prepared by well known, conventional techniques, 4.69 grams (0.005 mole) of phosphate ester halide reactant prepared as described in example 1, and 26 grams of water. The reaction mixture is heated at 90° C. for 3 hours at which time a clear, viscous, yellow solution is obtained having a % NaCl content of 1.9% (2.1 theoretical).

The resulting product added to water forms a clear solution which produces a stable foam.

EXAMPLE 3

A carboxyl containing (pendant) trimethylsilyl capped silicone fluid obtained from Shin Etsu under the designation X-223701E having a carboxyl content of 0.95% and initial equivalent weight of 4740 is used in this example.

967 grams (0.204 mole) of the above silicone fluid is combined with 31.2 grams (excess) of dimethylaminopropyl amine (DMAPA) and heated slowly under nitrogen to about 185° C. while volatiles coming off are collected. After a period of 4 hours, 15.5 ml of volatiles are collected as two layers, the bottom one being water with some volatilized DMAPA.

The reaction mixture having an acid number less than 1 is then heated to about 140° C. at 5 mm vacuum for 4 hours to produce a product having an alkali number of 11.4 and an equivalent weight of 4921.

9.8 grams (0.002 mole) of the above silicone/DMAPA reaction product are mixed with 2.4 grams (0.008 mole) of the cocyl sarcosine/DMAPA reaction product prepared as in example 1, 3.13 grams (0.0033 mole) of the phosphate ester halide reactant of example 2 and 29.5 grams water (30% solids concentration). The reaction mixture is heated for 3 hours at 94° to 95° C. during which time a clear but somewhat hazy solution is obtained. The % NaCl content of the reaction product is 1.4. The resulting product forms a clear solution when added to water which produces a large amount of stable foam.

EXAMPLE 4

Using the silicone/DMAPA reaction product of example 3 (equivalent weight of 4921) and the phosphate ester halide reactant of example 1, a series of mixtures of the two reactants in equivalent weight ratios ranging from 0.1 to 6:1 in water at solid content concentrations ranging from 10–70% are reacted. The various combination of reactants failed to form a homogeneous reaction mixture during reaction times ranging from 2 to 10 hours at temperatures up to 100° C. Similar results are obtained with the addition of cosolvents such as isopropanol and propylene glycol to the reaction system.

EXAMPLE 5

A reaction mixture is prepared from 39.2 grams of the silicone/DMAPA reaction product of example 3, 12 grams of a linoleic acid/DMAPA reaction product, 15.92 grams of the cocoyl sarcosine/DMAPA reaction product of example 1, 28.2 grams of the phosphate ester halide reactant of example 1 and 91.6 grams of water. The reaction mixture is heated to 90° C. for four hours during which time a clear solution is formed having a % NaCl content of 2.7.

EXAMPLE 6

Trisiloxane 1,1,1,3,5,5,5-hepta methyl, 3-Dimethylamino propyl trisiloxane prepared by the platinum catalyzed addition of the corresponding heptamethyltrisiloxane to N,N Dimethyl allyl amine as described in U.S. Pat. No. 3,658, 867 is used in this example. A reaction mixture containing 2.4 grams of the above trisiloxane (0.008 mole), 3.2 grams (0.012 mole) of cetyldimethylamine, 6.24 grams of the phosphate ester halide reactant of example 1, and 15 ml water is prepared and heated to 90° C. for 3 hours. A homogeneous, clear solution is formed having an alkali number less than 2.

A few drops of the product when added to 100 ml of water forms a clear solution which forms a stable foam when shaken. Although some preferred embodiments have been described, many modifications and variations may be made thereto in light of the above teachings. It is therefore to be understood that within the scope of the appended claims, the invention may be practiced otherwise than as specifically described and illustrated.

EXAMPLE 7

DiSodium 1,3 Bis 3 chloro-2 hydroxy propyl pyrophosphate is prepare by charging 446 Parts of $Na_4P_2O_7 10H_2O$ (1 mole) and 178 parts $H_4P_2O_7$ (1 mole) with 1000 parts deionized water to a reaction vessel and reacting the same with 320 parts epichlorohydrin at 60–80° C. for 3–4 hours. 81.4 parts (0.2 equivalents) of the above reaction product is combined with a mixture of a pendant trimethylsilyl silicone amidoamine having an equivalent weight of 1335 (0.05 equivalent) and 57.6 parts of N-Dimethylaminopropyl linoleamide (0.15 equivalents) and then diluted with 480 grams of water to a 30% concentration. After the solution is adjusted to a pH of 8, the reaction mixture is heated to 90–95° C. for a period of 4–5 hours at which time a clear solution forms. The reaction is monitored via argentometric estimation for covalent chloride to ionic chloride and the reaction is completed in 5 hours.

The reaction product foams well in water.

EXAMPLE 8

A 3-chloro-2 hydroxy propylester salt of phosphorous acid is prepared by charging 41 grams (0.5 mole) of phosphorus and, 409 grams of water and 50 grams of a 50% NaOH solution (0.6 mole) to a reaction vessel and warmed to 75° C. 46.25 grams (0.5 mole) of epichlorohydrin is then added and the reaction mixture is heated at 75° C. for 1½ hours with stirring.

196 parts of the combined epichlorohydrin-phosphite reaction mixture is admixed with a 50% sodium hydroxide solution to achieve a pH of 8 followed by adding the combination a pendant trimethylsilyl capped silicone amidoamine having an equivalent weight of 1335 (13.35 gram) and 27.3 parts of cocoyl sarcosine amidoamine (0.09 equivalents). The reaction mixture is diluted with water to achieve 25% solids.

The reaction mixture is heated to 90° C. for 2 hours whereupon a clear aqueous solution is formed.

EXAMPLE 9

3-Bromopropyl diacid phosphate ($BrCH_2CH_2CH_2OPO(OH)_2$) is prepared by reacting 3-Bromopropanol with $POCl_3$ utilizing one equivalent of triethyamine in methylene chloride solvent. The Dichloride is isolated and hydroyzed to the diacid with water. The pH of the product in water is adjusted to 8 followed by the addition of an equivalent amount of the 50:50 combination of a trimethylsilyl capped silicone amidoamine having an equivalent weight of 1335 and N-Dimethyl aminopropyl derivative of linoleamide. The reaction mixture is adjusted with water to 30% total solids.

The reaction mixture is heated for 4 hours at 90° C. A clear solution is formed.

What is claimed is:

1. Phospholipid compositions represented by the following general formula:

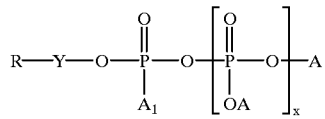

wherein:

A is selected from H, M, or R—Y—;

$A_1$ is selected from H, OH, OM or R—Y—O—;

x is 0 or an integer from 1 to 5;

M is a cation;

Y is alkylene or substitued alkylene; and

R is a mixture of quaternized organosilicone amine moieties selected from the group consisting of:

a) a quaternized organosilicone amidoamine moiety of the formula:

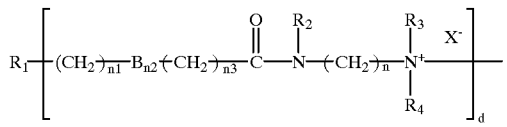

wherein:

$R_1$ is a silicone backbone chain to which amidoamine or amine functional group(s) can be attached;

$R_2$ is hydrogen or alkyl, hydroxyalkyl or alkenyl of up to 6 carbon atoms each, or cycloalkyl of up to 6 carbon atoms, or polyoxyalkylene of up to 10 carbon atoms within the oxyalkylene unit;

$R_3$ and $R_4$, which may be the same or different, are selected from alkyl, hydroxyalkyl, carboxyalkyl of up to 6 carbon atoms in each alkyl, or polyoxyalkylene of up to 10 carbon atoms; in addition $R_3$ and $R_4$ taken together with the nitrogen to which they are attached represent a N-heterocycle;

$X^-$ is an anion;

n is an integer from 2 to 12;

$n^1$ is zero or an integer from 1 to 12;

$n^2$ is 0 or 1;

$n^3$ is an integer from 1 to 5;

B is sulfur (S) or oxygen (O); with the proviso that when $n^2$ is 0, $n^1$ or $n^3$ is at least 1 and when $n^2$ is 1, $n^1$ and $n^3$ each is at least 1; and d is one or greater; and b) a quaternized organosilicone tertiary amine moiety of the formula:

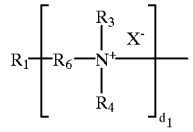

wherein:

$R_1$ is a silicone backbone claim to which amidoamine or amine functional groups can be attached;

$R_6$ is alkylene, hydroxyalkylene, arylene, alkarylene, aralkylene, heteroalkylene wherein the heteroatom can be N, S or O and there can be more than one of such hetero atoms in the chain;

$X^-$ is an anion;

$d^1$ is an integer of one or greater;

$R_3$ and $R_4$, which may be the same or different, are selected from alkyle, hydroxyalkyl, carboxyalkyl of up to 6 carbon atoms in each alkyl, or polyoxyalkylene of up to 10 carbon atoms; in addition $R_3$ and $R_4$ taken together with the nitrogen to which they are attached represent a N-heterocycle;

and a quaternized organic amine moiety selected from the group consisting of:

c) a quaternized organic amidoamine moiety of the formula:

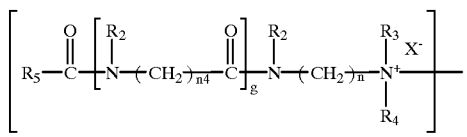

wherein:
R$_5$ is alkyl, alkenyl, alkoxyalkyl or hydroxyalkyl of from 5 to 21 carbon atoms each, alkaryl or aryl of up to 20 carbon atoms;
R$_2$ is hydrogen or alkyl, hydroxyalkyl or alkenyl of up to 6 carbon atoms each, cycloalkyl of up to 6 carbon atoms, or polyoxyalkylene of up to 10 carbon atoms within the oxyalkylene unit;
R$_3$ and R$_4$ which may be the same or different, are selected from alkyl, hydroxyalkyl, carboxyalkyl of up to 6 carbon atoms in each alkyl moiety, and polyoxyalkylene of up to 10 carbon atoms; in addition R$_3$ and R$_4$ taken together with the nitrogen to which they are attached represent an N-heterocycle;
X$^-$ is an anion;
g is 0 or 1;
n is integer from 2 to 12; and
n$^4$ is 1 or greater; and d) an organic quaternized tertiary amine moiety of the formula:

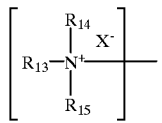

wherein:
R$_{13}$, R$_{14}$ and R$_{15}$ are the same or different and are alkyl, substituted alkyl, alkyl aryl or alkenyl groups of up to 16 carbon atoms with the proviso that the total carbon atoms in R$_{13}$+R$_{14}$+R$_{15}$ is between 10 and 24;

with the proviso that wherein R is a mixture of organosilicone amine and organic amine moieties, at least 5 equivalent weight percent to about 60 equivalent weight percent of the total equivalent weight of amine moieties of the phospholipid composition is a quaternized organosilicone amidoamine moiety, a quaternized organosilicone tertiary amine moiety or mixtures of the same.

2. The phospholipid compositions according to claim 1, wherein the silicone backbone chain R$_1$ to which amine functional group can be attached is of the formula:

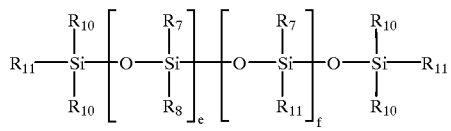

wherein:
R$_7$ and R$_8$, which may be the same or different are selected from alkyl, aryl, capped or uncapped polyoxyalkylene, alkaryl, aralkylene or alkenyl (vinyl);
R$_{10}$ can be the same or different and are selected from alkyl, aryl or olefinic (vinyl);
R$_{11}$, which can be the same or different, can be selected from R$_{10}$, —(CH$_2$)$_{n1}$—B$_{n2}$—(CH$_2$)$_{n3}$—CO—NR$_2$— (CH$_2$)$_n$—NR$_3$R$_4$, —R$_6$—NR$_3$R$_4$— and mixtures thereof, wherein R$_2$, R$_3$, R$_4$, R$_6$, B, n, n$^1$, n$^2$ and n$^3$ are as defined above; with the proviso that at least one of R$_{11}$ is an amidoamine or tertiary amine;
e can be an integer of O to 50,000;
f can be an integer of 0 to 100.

3. The phospholipid composition according to claim 2, wherein f is 0.

4. The phospholipid composition according to claim 2 wherein the terminal groups R$_{11}$ are R$_{10}$ and f is greater than 0.

5. The phospholipid compositions according to claim 1, wherein g in the quaternized organic amidoamine moiety c) is 1.

6. The phospholipid compositions according to claim 1, wherein R is a mixture of:
a) quaternized organosilicone amidoamine moieties of the formula:

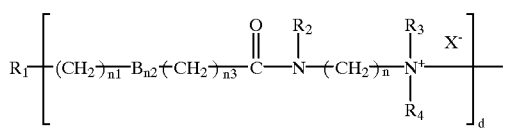

wherein:
R$_1$ is a silicone backbone chain to which amidoamine and/or amine functional group(s) can be attached;
R$_2$ is hydrogen or alkyl, hydroxyalkyl or alkenyl of up to 6 carbon atoms each, or cycloalkyl of up to 6 carbon atoms, or polyoxyalkylene of up to 10 carbon atoms within the oxyalkylene unit;
R$_3$ and R$_4$, which may be the same or different, are selected from alkyl, hydroxyalkyl, carboxyalkyl of up to 6 carbon atoms in each alkyl, or polyoxyalkylene of up to 10 carbon atoms;
X$^-$ is an anion;
n is an integer from 2 to 12;
n$^1$ is zero or an integer from 1 to 12;
n$^2$ is 0 or 1;
n$^3$ is an integer from 1 to 5;
B is sulfur (S) or oxygen (O); with the provision that when n$^2$ is 0, n$^1$ or n$^3$ is at least 1 and when n$^2$ is 1, n$^1$ and n$^3$ each is at least 1; and
d is one or greater; and c) quaternized organic amidoamine moieties of the formula:

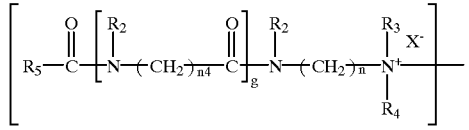

wherein:
R$_5$ is alkyl, alkenyl, alkoxy, alkyl or hydroxyalkyl of from 5 to 21 carbon atoms each, alkaryl or aryl of up to 20 carbon atoms;
R$_2$ is hydrogen or alkyl, hydroxyalkyl or alkenyl of up to 6 carbon atoms each, cycloalkyl of up to 6 carbon atoms, or polyoxyalkylene of up to 10 carbon atoms within the oxyalkylene unit;
R$_3$ and R$_4$ which may be the same or different, are selected from alkyl, hydroxyalkyl, carboxyalkyl of up to 6 carbon atoms in each alkyl moiety, or polyoxyalkylene of up to 10 carbon atoms; in addition $R_3$ and $R_4$ taken together with the nitrogen to which they are attached represent an N-heterocycle;

$X^-$ is an anion;

g is 0 or 1;

n is integer from 2 to 12;

$n^4$ is 1 or greater.

with the proviso that at least 5 equivalent weight percent to about 60 equivalent weight percent of the total equivalent weight of amine moieties of the phospholipid composition is a quaternized organosilicone amidoamine moiety or mixtures of the same.

7. The phospholipid compositions according to claim 6, wherein the silicone backbone chain $R_1$ to which amine functional group can be attached is of the formula:

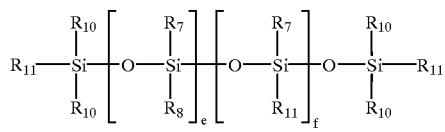

wherein:

$R_7$ and $R_8$, which may be the same or different are selected from alkyl, aryl, capped or uncapped polyoxyalkylene, alkaryl, aralkylene or alkenyl (vinyl);

$R_{10}$ can be the same or different and is selected from alkyl, aryl or olefinic (vinyl);

$R_{11}$, which can be the same or different, is selected from $R_{10}$, $-(CH_2)_{n1}-B_{n2}-(CH_2)_{n3}-CO-NR_2-(CH_2)_n-NR_3R_4$, $-R_6-NR_3R_4-$ or mixtures thereof, wherein $R_2$, $R_3$, $R_4$, $R_6$, B, n, $n^1$, $n^2$ and $n^3$ are as defined above; with the proviso that at least one of $R_{11}$ is an amidoamine;

e can be an integer of 0 to 50,000;

f can be an integer of 0 to 100.

8. The phospholipid compositions according to claim 6, wherein g in the quaternized organic amidoamine moiety c) is 1.

9. The phospholipid composition according to claim 7, wherein f is 0.

10. The phospholipid composition according to claim 7, wherein the terminal groups $R_{11}$ are $R_{10}$ and f is greater than 0.

11. The phospholipid composition according to claim 1, wherein Y is $-CH_2-CHOH-CH_2-$.

12. A method of preparing novel phospholipid compositions according to claim 1 represented by the general formula:

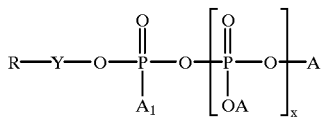

wherein:

A is selected from H, M, or R—Y—;

$A_1$ is selected from H, OH, OM or R—Y—O—;

x is 0 or the intefer from 1 to 5;

M is a cation;

Y is alkylene or substituted alkylene; and

R is a mixture of quaternized amidoamine and/or tertiary amine moieties as hereinabove defined;

which comprises reacting the combination of an organic amidoamine organic tertiary amine reactant or mixture of the same and a silicone modified amidoamine silicone modified tertiary amine reactant or mixtures of the same with a polyphosphate, phosphite or phosphate ester halide reactant in the equivalent weight ratios of from about 0.7 to 3.3, of total amidoamine or tertiary amine reactants to 1 of polyphosphate, phosphite or phosphate ester halide reactant until the amine reactant is completely reacted, with the proviso that at least 5 equivalent weight percent to about 60 equivalent weight percent of the total equivalent weight of amine reactants will be silicone containing, said polyphosphate, phosphite or phosphate ester halide reactant being of the general formula:

$$X-Y-O-\underset{A_3}{\overset{\overset{O}{\|}}{P}}-O-\left[\underset{OA_2}{\overset{\overset{O}{\|}}{P}}-O\right]_x-A_2$$

wherein:

$A_2$ is selected from H, M and X—Y—;

$A_3$ is selected from H, OH, OM and X—Y—O—;

x is 0 or the integer from 1 to 5;

M is a cation;

Y is alkylene or substituted alkylene; and

X is halogen.

* * * * *